US008455010B1

(12) United States Patent
Norton et al.

(10) Patent No.: US 8,455,010 B1
(45) Date of Patent: *Jun. 4, 2013

(54) PRODUCT AND METHOD FOR PRODUCING AN IMMUNE SYSTEM SUPPLEMENT AND PERFORMANCE ENHANCER

(75) Inventors: Verdis Norton, Sandy, UT (US); Gary L. Samuelson, Sandy, UT (US)

(73) Assignee: Reoxcyn Discoveries Group, Inc, Sandy, UT (US)

( * ) Notice: Subject to any disclaimer, the term of this patent is extended or adjusted under 35 U.S.C. 154(b) by 576 days.

This patent is subject to a terminal disclaimer.

(21) Appl. No.: 12/592,402

(22) Filed: Nov. 24, 2009

Related U.S. Application Data

(63) Continuation-in-part of application No. 12/383,212, filed on Mar. 20, 2009, now Pat. No. 8,367,120, which is a continuation-in-part of application No. 12/290,398, filed on Oct. 30, 2008, now abandoned.

(60) Provisional application No. 61/001,101, filed on Oct. 31, 2007.

(51) Int. Cl.
| | |
|---|---|
| *A61K 33/20* | (2006.01) |
| *A61K 33/40* | (2006.01) |
| *A61K 33/14* | (2006.01) |
| *A01N 59/08* | (2006.01) |

(52) U.S. Cl.
USPC ............................ 424/615; 424/665; 424/680

(58) Field of Classification Search
None
See application file for complete search history.

(56) References Cited

U.S. PATENT DOCUMENTS

| | | |
|---|---|---|
| 1,029,580 A | 6/1912 | Bane |
| 1,200,165 A | 10/1916 | Burgess |
| 2,473,986 A | 6/1949 | Booth |
| 2,985,514 A | 5/1961 | Lundeen |
| 3,234,110 A | 2/1966 | Beer |
| 3,365,061 A | 1/1968 | Bray |
| 3,505,215 A | 4/1970 | Bray |
| 3,622,479 A | 11/1971 | Schneider |
| 3,654,148 A | 4/1972 | Bradley |
| 3,749,524 A | 7/1973 | Jordan |
| 3,791,768 A | 2/1974 | Wanner |
| 3,825,122 A | 7/1974 | Taylor |
| 3,996,126 A | 12/1976 | Rasmussen |
| 4,000,065 A | 12/1976 | Ladha et al. |
| 4,019,986 A | 4/1977 | Burris et al. |
| 4,070,280 A | 1/1978 | Bray |
| 4,077,883 A | 3/1978 | Bray |
| 4,124,488 A | 11/1978 | Wilson |
| 4,138,210 A | 2/1979 | Avedissian |
| 4,151,092 A | 4/1979 | Grimm et al. |
| 4,187,173 A | 2/1980 | Keefer |
| 4,288,326 A | 9/1981 | Keefer |
| 4,290,873 A | 9/1981 | Weaver |
| 4,306,952 A | 12/1981 | Jansen |
| 4,367,140 A | 1/1983 | Wilson |
| 4,389,311 A | 6/1983 | La Freniere |
| 4,434,056 A | 2/1984 | Keefer |
| 4,534,713 A | 8/1985 | Wanner |
| 4,560,455 A | 12/1985 | Porta et al. |
| RE32,077 E | 2/1986 | deNora et al. |
| RE32,144 E | 5/1986 | Keefer |
| 4,613,415 A * | 9/1986 | Wreath et al. ................. 205/335 |
| 4,632,754 A | 12/1986 | Wood |
| 4,710,233 A | 12/1987 | Hohmann et al. |
| 4,722,263 A | 2/1988 | Valentin |
| 4,756,830 A | 7/1988 | Fredkin |
| 4,759,844 A | 7/1988 | Lipschultz et al. |
| 4,761,208 A | 8/1988 | Gram et al. |
| 4,786,380 A | 11/1988 | van Duin et al. |
| RE33,135 E | 12/1989 | Wanner, Sr. et al. |
| 5,085,753 A | 2/1992 | Sherman |
| 5,207,916 A | 5/1993 | Goheen et al. |
| 5,221,451 A | 6/1993 | Seneff et al. |
| 5,244,579 A | 9/1993 | Horner et al. |
| 5,306,428 A | 4/1994 | Tonner |
| 5,316,740 A | 5/1994 | Baker et al. |
| 5,320,718 A | 6/1994 | Molter et al. |
| 5,334,383 A | 8/1994 | Morrow |
| 5,354,264 A | 10/1994 | Bae et al. |
| 5,358,635 A | 10/1994 | Frank et al. |
| 5,385,711 A | 1/1995 | Baker et al. |
| 5,496,466 A | 3/1996 | Gray |
| 5,503,736 A | 4/1996 | Schoenmeyr |
| 5,507,932 A * | 4/1996 | Robinson ................ 204/230.2 |
| 5,531,887 A | 7/1996 | Miers |
| 5,534,145 A | 7/1996 | Platter et al. |
| 5,540,848 A | 7/1996 | Engelhard |
| 5,558,762 A | 9/1996 | Fife et al. |
| 5,560,816 A | 10/1996 | Robinson |
| 5,581,189 A | 12/1996 | Brenn |
| 5,597,482 A | 1/1997 | Melyon |
| 5,622,848 A | 4/1997 | Morrow |
| 5,674,537 A | 10/1997 | Morrow |

(Continued)

FOREIGN PATENT DOCUMENTS

| | | |
|---|---|---|
| EP | 89830309.4 | 4/1989 |
| EP | 2078700 | 12/2008 |

(Continued)

OTHER PUBLICATIONS

Gomes et al. (J. Biochem. Biophys. Methods 2005, 65, 45-8).*

(Continued)

*Primary Examiner* — James H Alstrum Acevedo
*Assistant Examiner* — Jessica Kassa
(74) *Attorney, Agent, or Firm* — K&L Gates LLP; Louis C. Cullman; Brian J. Novak

(57) ABSTRACT

A balanced redox-signaling compound with reactive molecules that mimic those naturally occurring inside cells that have been precisely stabilized and formulated as a supplement for oral consumption acting to enhance proper immune system function, enhance the efficiency and production of the body's native antioxidants as well as enhance the performance of intercellular communications involved in healthy tissue maintenance and athletic performance.

11 Claims, 1 Drawing Sheet

U.S. PATENT DOCUMENTS

| | | | |
|---|---|---|---|
| 5,685,980 A | 11/1997 | Patapoff et al. | |
| 5,725,758 A | 3/1998 | Chace et al. | |
| 5,731,008 A | 3/1998 | Morrow | |
| 5,928,490 A | 7/1999 | Sweeney | |
| 5,958,229 A | 9/1999 | Filiopoulos et al. | |
| 5,989,396 A | 11/1999 | Prasnikar et al. | |
| 6,007,686 A | 12/1999 | Welch et al. | |
| 6,056,666 A | 5/2000 | Williams | |
| 6,106,691 A | 8/2000 | Nakamura et al. | |
| 6,110,424 A | 8/2000 | Maiden et al. | |
| 6,117,285 A | 9/2000 | Welch et al. | |
| 6,261,464 B1 | 7/2001 | Herrington et al. | |
| 6,309,523 B1 | 10/2001 | Prasnikar et al. | |
| 6,514,401 B2 | 2/2003 | Chyou et al. | |
| 6,524,475 B1 | 2/2003 | Herrington et al. | |
| 6,632,336 B2 | 10/2003 | Kasuya | |
| 6,632,347 B1 | 10/2003 | Buckley et al. | |
| 6,736,966 B2 | 5/2004 | Herrington et al. | |
| 6,964,739 B2 | 11/2005 | Boyd et al. | |
| 7,008,523 B2 | 3/2006 | Herrington | |
| 7,087,766 B2 * | 8/2006 | Nagano et al. | 549/223 |
| 2004/0195090 A1 | 10/2004 | Omasa | |
| 2006/0039996 A1 * | 2/2006 | Palmer | 424/661 |
| 2006/0076248 A1 * | 4/2006 | Kindred | 205/743 |
| 2006/0137973 A1 | 6/2006 | Herrington | |
| 2006/0157343 A1 | 7/2006 | Herrington | |

FOREIGN PATENT DOCUMENTS

| | | |
|---|---|---|
| KR | 20020074262 | 9/2002 |
| WO | PCT/US82/00811 | 1/1983 |
| WO | PCT/US98/06769 | 10/1998 |
| WO | PCT/US00/21279 | 8/2000 |
| WO | PCT/US01/48747 | 12/2001 |

OTHER PUBLICATIONS

Removal and Inactivation of *Staphylococcus epidermidis* Biofilsm by Electrolysis by C. Rabinovitch and P. Stewart, Montana State U Feb. 23, 2006 vol. 72, No. 9, p. 6364.

Center for Biofilm Engineering, Proceedings Winter 2004, CBE Technical Advisory Conference Feb. 5-6 Montana State U.

* cited by examiner

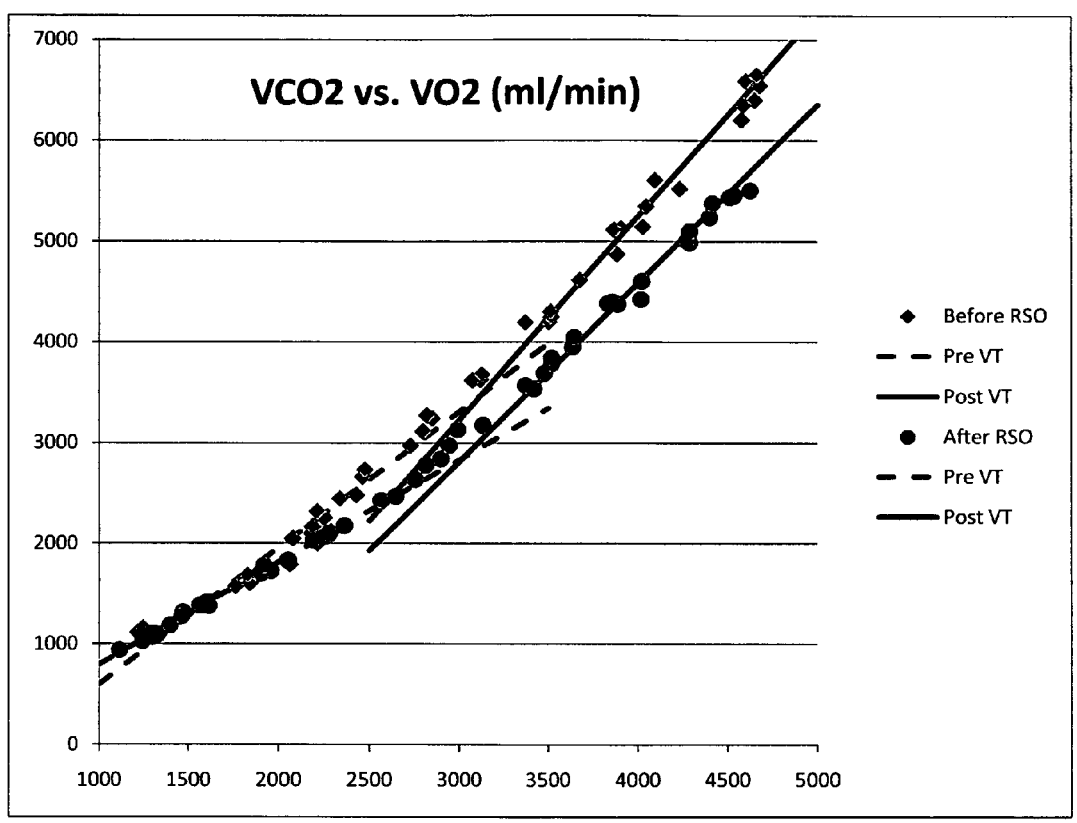

PRODUCT AND METHOD FOR PRODUCING AN IMMUNE SYSTEM SUPPLEMENT AND PERFORMANCE ENHANCER

RELATED APPLICATIONS

This application is a continuation-in-part patent application of the continuation-in-part patent application entitled "Method and Apparatus for Producing a Stabilized Antimicrobial Non-toxic Electrolyzed Saline Solution Exhibiting Potential as a Therapeutic" filed Mar. 11, 2009, Ser. No. 12/383,212, which is a continuation-in-part patent application of the continuation-in-part patent application entitled "Method and Apparatus for Producing a Stabilized Antimicrobial Non-toxic Electrolyzed Saline Solution Exhibiting Potential as a Therapeutic" filed Oct. 30, 2008, Ser. No. 12/290,398, abandoned, based on the provisional patent application entitled "Method and Apparatus for Producing an Electrolyzed Saline Solution Exhibiting Anti-infective Potential as a Therapeutic" filed Oct. 30, 2007 as Ser. No. 61/001,101, abandoned.

BACKGROUND OF THE INVENTION

1. Field

This invention pertains to health immune supplements. More particularly it pertains to a product and electrochemical method processing saline solutions to produce a balanced redox-signaling compound with reactive signaling molecules that mimic those naturally occurring inside one's cells. These molecular compounds are precisely stabilized and formulated as a supplement for oral consumption acting to enhance proper immune system function, enhance the efficiency and production of the body's native antioxidants as well as enhance the performance of intercellular communications involved in healthy tissue maintenance and athletic performance.

2. Prior Art

There are a number of methods to electrochemically produce reactive signaling molecules. Electrolysis of saline solutions has long been used to produce antimicrobial solutions. Some examples include methods to produce chlorinated water, bleach and hydrogen peroxide. Typically, the methods and apparatus used to electrolyze these solutions employ ion-selective barriers between the electrodes in order to efficiently isolate the target molecules and eliminate unwanted byproducts. A fundamentally different method and apparatus for producing a non-toxic antimicrobial electrolyzed saline solution is disclosed in the parent application discussing eight United States patents, and two Japanese patents and a Mexican patent. These eleven patents cover various applications for electrolyzed saline solution, the machinery that manufactures it, and the method by which it is manufactured.

They typically have produced measurably different variations of electrolyzed saline solution. Each variation, however, exhibited some antimicrobial action and many of these devices produced solutions with measurable amounts of the components (chlorine, pH, ozone, etc.). The resulting electrolyzed saline compositions, however, have not historically been satisfactorily consistent or controllable with respect to the concentrations of Reactive Oxygen Species (ROS). In addition, these prior patents could produce toxic chemicals (chlorates) in the process of electrolyzing the saline solution.

Consequently, there is a need for an improved manufacturing method, such as that described below, to consistently produce solutions suitable as an immune system supplements and performance enhancers in humans and warm-blooded animals.

SUMMARY OF THE INVENTION

The invention comprises a method to produce a balanced formulation of stabilized redox-signaling molecules that is particularly safe and suited for oral consumption, hereafter called the Redox Signaling Oral (RSO) Compound. This formulation is similar to that of a target composition of redox-signaling molecules that exists naturally inside a healthy human cell. The RSO compound acts to enhance proper immune system function, to enhance the efficiency and production of the body's native antioxidants as well as to enhance the performance of intercellular communications involved in the maintenance of healthy tissues and athletic performance.

Redox signaling deals with the action of a set of several simple reactive signaling molecules that are mostly produced by the mitochondria residing inside human cells during the metabolism of sugars. These reactive signaling molecules are categorized into two general groups, Reactive Oxygen Species (ROS) [containing oxidants] and Reduced Species (RS) [containing reductants]. These fundamental universal signaling molecules in the body are the simple but extremely important reactive signaling molecules that are formed from combinations of the atoms (Na, Cl, H, O, N) that are readily found in the saline bath that fills the inside of the cells (cytosol). All of the molecular mechanisms inside healthy cells float around in this saline bath and are surrounded by a balanced mixture of such reactive signaling molecules. A few examples of the more than 20 reactive molecules formed from these atoms inside the cell, some of which are discussed in the parent application, are superoxide, hydrogen peroxide, hypochlorous acid and nitric oxide.

Such reactive signaling molecules are chemically broken down by specialized enzymes placed at strategic locations inside the cell. Some of these protective enzymes are classified as antioxidants such as Glutathione Peroxidase and Superoxide Dismutase. In a healthy cell, the mixtures of these reactive signaling molecules are broken down by the antioxidant enzymes at the same rate that they are produced by the mitochondria. As long as this homeostatic balance is maintained, the cell's chemistry is in balance and all is well.

When damage occurs to the cell, for any number of reasons, including bacterial or viral invasion, DNA damage, physical damage or toxins, this homeostatic balance is disturbed and a build-up of oxidants or reductants occurs in the cell. This condition is known as oxidative stress and it acts as a clear signal to the cell that something is wrong. The cell reacts to this signal by producing the enzymes and repair molecules necessary to attempt repairs to the damage and it also can send messengers to activate the immune system to identify and eliminate threats. If oxidative stress persists in the cell for more than a few hours, then the cell's repair attempts are considered unsuccessful and the cell kills and dismantles itself and is replaced by the natural cellular division of healthy neighboring cells.

On a cellular level, this is essentially the healthy tissue maintenance process: damaged cells are detected and repaired or replaced by healthy cells. This cellular repair and regeneration process is constantly taking place, millions of times an hour, in all parts of the body.

The method for producing a balanced foundational product to allow the body and immune system to better function, comprises first determining a balanced target mixture of redox-signaling molecules inherent to healthy cells and measuring the concentrations of the reactive molecules contained therein, usually with fluorescent indicators.

This target mixture is then replicated by the electrochemical method of the parent patent application in a process starting with a combination of pure water and salt (NaCl) that undergoes a specific electrochemical processing where the process parameters (temperature, flow, pH, power-source modulation and salt homogeneity and concentration) are varied to produce the ultimate specific target formulation.

The resulting formulation typically has less than about 10% of the recommended daily allowance (RDA) of sodium (usually between 115 mg to 131 mg of sodium per 4 fl. oz. serving) and a pH of between 7.2 and 7.5 with total chlorine less than 40 ppm. These ranges also make the product palatable (won't cause nausea) when taken in 8 oz or larger quantities. The sodium chloride concentration is a variable parameter that can be upwardly adjusted and still produce the desired target composition of the final RSO Compound mixture at the expense, of course, of becoming less palatable.

During the electrochemical process, to insure that the saline solution is well mixed, usually homogenizing means are included, such as a fluid circulation device to maintain flow aging stratification and homogeneity of the saline solution during electrolysis.

Next, the temperature and flow of the circulating saline is adjusted to a level to prevent production of chlorates and produce the desired relative concentrations of resulting chemical redox specie components during electrolysis using the apparatus and method disclosed in the parent application. The resultant redox specie components are then measured with the same indicators used to measure the balance of ROS and RS and the other chemical characteristics of the target mixture mentioned above. This process may involve an iterative process where the temperature, flow and other parameters are adjusted until a composition similar to that of the target mixture is achieved.

The resultant RSO mixture of reactive signaling molecules is stable with many of its components measurable using standard analytic methods. As discussed above, such signaling molecules are the same as those that are naturally produced inside of living cells and are measured using standard laboratory methods, such as the employment of certain fluorescent dyes that act as indicators. The concentration of some of the individual components of the RSO Compound is thus tested and verified in the laboratory.

For example, by regularly utilizing three standard fluorescent indicators, namely R-Phycoerythrin (R-PE), Aminophenyl fluorescein (APF) and Hydroxyphenyl fluorescein (HPF) their corresponding redox specie components can be tracked. Such fluorescent indicator molecules change brightness when they come into contact with specific redox specie. These indicator dyes are very resistant to false positives and are well studied. Such change in fluorescence is then measured using a fluorospectrometer. The change in fluorescence of these indicators quantifies the existence and relative concentration of their corresponding redox specie.

A combination of measurements from these indicators can be utilized to measure the concentration of reactive redox signaling molecules in the test RSO Compound and thereby the relative concentration of its major reactive molecular components. Several types of laboratory equipment and methods can also be employed to determine the composition of the proper target solution and that of the resultant electrolyzed RSO Compound. One such method is by the proper employment of a Nanodrop™ 3300 fluorospectrometer, made by Thermo Fischer Scientific, along with the R-PE, APF and HPF fluorescent dyes to measure the relative concentrations of reactive signaling molecules inside test RSO Compounds. Such measurements can then be compared to measurements taken from a desired target solution. Typically the test RSO Compound is measured along-side the desired target solution.

In one such method, the concentration and presence of such reactive molecules is verified when the three indicators, R-PE, APF and HPF show 1) that a 2 micro molar concentration of R-PE loses 5%-50% of its fluorescence 6 hours after a 1:1000 solution of the RSO is added; 2) and R-PE measurements indicate the same fluorescence levels as a standard ROS generating solution of 0.2 to 1.0 mM AAPH, and 3) the APF measurements indicate the same relative amount as the target compound and 4) HPF measurements indicate a negligibly small reading and 5) the pH is between 7.2 and 7.5 and 6) the total chlorine is less that 35 ppm by weight.

Once the required electrolytic operating parameters are determined for producing the desired RSO Compound, the electrochemical device is then activated and adjusted to oxidize and reduce the saline solution in such a way as to produce an RSO Compound with similar concentration and mixture of reactive molecules as those present in the healthy target living cells.

The resultant RSO Compound is then administered orally or topically to a human as a supplement for the natural redox-signaling compounds formed inside the cells to enhance proper immune system function, to enhance the efficiency and production of the body's native antioxidants as well as to enhance the performance of intercellular communications involved in healthy tissue maintenance and athletic performance.

In summary, the composition of the redox-signaling RSO Compound is produced by utilizing an electrochemical process wherein the process parameters (temperature, flow, pH, power-source modulation and salt homogeneity and concentration) are varied until certain chemical indicators measure the same relative composition as compared to a target composition similar to that produced in the cells. The method and RSO Compound produced therefrom, thus provides a redox-signaling compound with reactive molecules that mimic those naturally occurring inside one's cells.

Summary of Research to Support Claims

The resultant RSO Compound produced by the above method was tested to determine its efficacy by independent research. An in-vitro scientific investigation was done in conjunction with a prominent national laboratory to determine the bioactivity of this redox-signaling RSO Compound on eukaryotic cells in a controlled environment. The following is a summary and explanation of the experimental results related to the action of the RSO Compound in contact with living human cells. The first part of this investigation was designed to determine if there was a possible toxic response due to contact of the RSO Compound with the cells.

When a cell is stressed by a toxin, the cell responds by sending a certain set of transcription factors into the nucleus. Once inside the nucleus, these transcription factors activate the genes responsible for cellular defense and protection against toxins (such as the inflammatory response). The translocation of certain transcription factors into the nucleus can be seen under a fluorescent microscope when the cells are stained by specific indicator dyes.

If the cell undergoes a toxic response, the fluorescent dye is pulled into the nucleus along with the transcription factor. In this experiment two transcription factors, the p65 subunit of NF-kappaB and P-Jun, were monitored. These two transcription factors are known to be activated in all toxic responses. In the photographs from the fluorescent microscopic images of the cells, a toxic response is registered if the green dye is seen to move into the nucleus.

Experimental Procedure: The target eukaryotic cells were cultured in dishes and exposed respectively to (1) Phosphate Buffered Saline (PBS)—the negative control (no toxic response expected), (2) 5% of the RSO Compound—Equivalent to replacing 5% of the nutrient solution (blood plasma) with the RSO Compound, (3) 20% of the RSO Compound—Equivalent to replacing 20% of the nutrient solution with the RSO Compound, and (4) A known toxin—the positive control (toxic response expected).

The response of the transcription factors, the p65 subunit of NF-kappaB and P-Jun, were photographed under a microscope after exposure to the four solutions listed above. A DAPI stain was also applied to the nuclei in order to help computer software to find the nucleus in the pictures. The software automatically tallied the amount of dye in the nuclei. In the case of P-Jun, measurements of over one hundreds cells were made in order to compile the summary data.

Results for P65/NF-kappaB:

In the images cells with stained for the p65 subunit of NF-kappaB, it is visually evident that no toxic response is registered for exposure of the cells to the RSO Compound compared to the clear positive response is seen in the positive control. The p65 subunit remains on the outside of the nuclei in images of cells with the RSO Compound, indicating that no NF-kappaB translocation is detected. There was no toxic response registered by the cells.

Results for P-Jun:

As reinforcement of the NF-kappaB results, the P-Jun data also shows visual evidence of no toxic response. It was necessary for the P-Jun data to be averaged over more than 100 cells in order to get statistically significant numerical results. The results clearly show that no significant toxicity exists for the 5% RSO Compound and only marginal response for the 20% the RSO Compound. Blood concentration for oral doses, however, will never get anywhere near even 1%.

These results are especially interesting considering that large concentrations of almost any compound (including pure water) are known to cause a toxic response in these same kinds of experiments. The non-toxic nature of the RSO Compound might be explained by the fact that protective enzymes found in eukaryotic cells are able to neutralize a redox-balanced mixture of reactive signaling molecules, such as that which is found natively inside the cells. The RSO Compound contains such a balanced mixture. These observations reinforce the zero-toxicity results of over 10 years of comprehensive toxicity testing done on previous formulations which were produced by similar electrochemical methods.

In the second part of this in-vitro investigation, live cells in culture dishes were exposed to the RSO Compound and the bioactivity regarding antioxidant activity of Glutathione Peroxidase (GPx) and Superoxide Dismutase (SOD) as well as the increase in the native production of these antioxidants inside cells was measured.

Experimental Methods for Antioxidant Activity: cells were cultured in several dishes with a bovine serum growth medium. As a primary measure, mouse epithelial-like cells were cultured (these cells react similarly to human cells in most cases) and later human endothelial cells were used to obtain relevant quantitative results.

In the antioxidant enhancement tests, some of the cell cultures were exposed to the RSO Compound and others cultures to the same amount of an inert phosphate buffered saline solution (PBS). The antioxidant activity of the cells in each was measured by a purchased kit, Array Design Stressgen kit (#900-158 for GPx activity and #900-157 for SOD activity). The chemical reagents inside these kits measure the ability of the antioxidants in the cell extracts to reduce oxidant activity that occurs naturally when certain oxidizing biological chemicals are added.

Results of Antioxidant Activity Tests:

The first results obtained showed large, well-defined effects. The cell extracts exposed to the RSO Compound exhibited eight (8) times the antioxidant efficiency for GPx that those exposed to the inert PBS. The SOD antioxidant efficiency was slightly less, with about 3 to 5 times enhancements in efficiency. Of note, this efficiency was evident especially at low level concentrations of the RSO Compound, tested down to 2.5% of full strength. Increasing the concentration of the RSO Compound at high concentrations did not notably increase the antioxidant efficiency; thus there appears to be a very low saturation threshold at low concentrations of GPx. There was some variability in the SOD efficiency tests with SOD concentration that made the confidence level for the accuracy of these tests lower.

It is safe to say that at least a 500% improvement in the overall antioxidant efficiency was seen during these preliminary in vitro tests due to exposure to the RSO Compound.

Experimental Methods for Antioxidant Up-regulation: in these experiments, some cultured human endothelial cells were exposed to the RSO Compound and others only to an inert phosphate buffer solution (PBS). Standard Western Blot analysis on all cells was done to determine if exposure to the RSO Compound activated the nucleus to call for increased production of antioxidants, such as GPx. The concentrations of transcription factors (messengers) in the nucleus that call for up-regulation of antioxidants were also measured in human endothelial cells and compared to cells that had not been exposed to the RSO Compound.

Results for Antioxidant Production:

The results for these tests were extraordinary in several regards. First, there was a slight, 5 to 10%, but real, up-regulation of anti-oxidant production in cells exposed to the RSO Compound. This effect was temporary, lasting only about 120 minutes but was clearly visible. The most interesting result, however, is that exposure to the RSO Compound at any concentration did not invoke the normal inflammatory transcription factor (NF-kappaB) and yet did invoke the antioxidant transcription factor (NRF2). Stimulating the production of antioxidants without stimulation of low-level inflammation is very rare and has stirred some interest in the scientific community.

With the antioxidant up-regulation transcription factor NRF2, positive movement of this transcription factor was seen in both the cells exposed to the RSO Compound and in the positive control. Averages over hundreds of cells were observed in order to obtain these results. These results were also verified by the Western Blot analysis showing clear responses in the increase of antioxidants upon exposure to the RSO Compound relative to the PBS saline control.

It is generally established that such increased efficiency in antioxidant action and production as well as activation of the cell's innate protective responses (especially without inflammatory responses) slows down the tissue aging process and results in more efficient healthy cellular maintenance processes.

Athletic Testing

In addition to the in vitro testing, tests were also run on athletes to determine if oral consumption of the RSO Compound has any effect on the ability of athletes to perform. Experimental Methods for Athletic Testing: seventeen (17) Athletes performed a $VO_2$max test where heart rate (HR), oxygen intake ($VO_2$), Carbon Dioxide outflow ($VCO_2$) and Ventilatory Threshold (VT), explained below, measured during a standard professionally administered $VO_2$max endurance test. Athletes were selected based on their physical condition and commitment to follow the rules during the test including maintaining their normal daily routines during the test period and faithfully drinking the RSO Compound during the 14 day test period. All abstained from drinking the RSO Compound for at least a week before the initial baseline testing.

The athletes took the baseline test the week before taking the RSO Compound. The final test was then done after orally taking the RSO Compound (4 oz. per day) for more than 14 days. Each athlete drank 8 oz of the RSO Compound immediately before taking the final test. The VO2max tests were performed on a CardioCoach® system by technicians having more than 5 years experience of administering VO2max tests on this system. The results were then analyzed using standard statistical methods for determining Ventilatory Threshold (VT).

During the baseline $VO_2$max test, the power output level of the athlete was recorded (the resistance level of the cycle or the speed and incline of the treadmill). This information was used to repeat the same power levels during the final test, making the final test, as far as power output, a repeat of the initial baseline test. If the athlete's endurance allowed, the test then was continued at a higher power output until $VO_2$max was detected.

Physiological Explanation of VT Endurance Measurements: For this experiment, the focus was placed on measuring Ventilatory Threshold (VT), which is widely recognized as a better and more accurate way to measure endurance and power output capacity than $VO_2$max itself. The VT can be measured by comparing the volume of oxygen intake ($VO_2$) to the volume of Carbon Dioxide exhaled ($VCO_2$). As the muscles put out more power, their demand for oxygen from the blood grows proportionally to the amount of waste $CO_2$ they expel into the blood. This is reflected in the $VO_2$ and $VCO_2$ measurements.

The body can be thought of as a machine: oxygen ($O_2$) goes into the lungs, passes into the blood where it is pumped into the muscle tissues. There it is combined with sugars and fats to produce the energy needed to sustain the power output. The waste products of aerobic energy production include carbon dioxide ($CO_2$). $CO_2$ is passed back out of the tissues into the lungs where it is then expelled. The amount of $O_2$ going in during aerobic exercise should be directly proportional to the $CO_2$ expelled; this is seen as a line on a graph comparing $VCO_2$ to $VO_2$ shown in FIG. 1.

There comes a point, however, during the $VO_2$max test that the power output of the muscles exceeds the ability of the lungs and heart to supply the needed oxygen. At this point an anaerobic process inside the muscle tissues begins to produce energy (energy without oxygen) in order to supply the energy deficit. The waste products of this process include excess lactic acid and an additional amount of $CO_2$. This anaerobic $CO_2$ waste, combined with the aerobic $CO_2$ waste can be measured as a much increased $VCO_2$ measurement relative to the $VO_2$. This point (VT) can be seen on the $VCO_2$ vs. $VO_2$ FIG. 1 graph as a "kink" as the volume of $CO_2$ being expelled goes quickly up to a higher level.

VT is defined as the point where $VCO_2$ starts its steeper incline. Thus VT marks the end of pure aerobic energy producing process and the beginning of a mixture of aerobic and anaerobic energy producing processes. This can also be measured with a sharp increase of lactic acid in the blood (usually denoted LT, Lactic Threshold). In this experiment LT was not measured. As lactic acid builds up in the tissues, it inhibits the ability of the tissues to absorb oxygen efficiently, making the aerobic process less efficient. At the Anaerobic Threshold (AT), the build-up of lactic acid begins to spiral up out of control. A few minutes after AT, the carbohydrate supply also runs out and the muscle tissue fails to function. This point of complete exhaustion typically comes several tens of seconds after $VO_2$max, (the point where the body is taking in the maximum amount of $O_2$ possible).

VO2max depends on a lot of genetic factors such as lung capacity, heart capacity and the efficiency of the air-blood interface to exchange $O_2$ and $CO_2$ in the lungs as well as the efficiency of the blood-tissue interface in the muscles. Normally VO2max will only significantly increase if lung or heart capacity increases due to long periods of strenuous exercise. VT, on the other hand, is a measure of how much power an athlete is able to sustain at his peak aerobic efficiency. VT can be increased if the blood-air interface in the lungs or blood-tissue interface becomes more efficient in transporting oxygen or getting rid of $CO_2$ and lactic acid. Thus VT is a parameter that it makes sense to target for increase in athletic training.

Results of the $VO_2$max Testing:

The results of the test are presented in summary form. Average Heart Rate (HR), Average VT, Average $VO_2$max and Average Time to achieve $VO_2$max are reported. Due to experimental error (a loose breathing mask, perhaps), the results for two athletes had to be removed from the averages for VT and $VO_2$max (averaged over 15 athletes). Averages for Heart Rate and Total Time are based on all 17 athletes.

The following table gives a summary of the results over all tested athletes as already explained. There is a statistical variance of about 3% on the VT averages, similar uncertainties should apply to all these averages:

| Averages | Before RSO Compound | After RSO Compound | % Change |
|---|---|---|---|
| VT (secs) | 306 | 344 | +12% |
| $VO_2$max (ml/kg/min) | 62.5 | 63.6 | +3% |
| Heart Rate (bpm) | 137 | 134 | −2% |
| Time to $VO_2$max (secs) | 639 | 703 | +10% |

Heart Rate is only measured over comparable regions, as to only compare heart rates at similar power output.

Observations and Conclusions Based on Results: there is a clear and unequivocal trend in the $VO_2$max data. Based on the data, about 70% of the athletes that took the RSO Compound experienced the ability to maintain a higher power output without crossing the Ventilatory Threshold (VT) that instigates fatigue, allowing them to go longer at the same power burn or to operate at a higher power burn than possible before taking the RSO Compound. This is based on the most salient feature of the data—the extension of time at similar power levels before the VT and $VO_2$max fatigue-related thresholds set in. These results deserve more careful investigation and verification.

Since 14 days do not give the body enough time to increase lung capacity or cardiovascular capacity, it seems reasonable to conclude that these trends may be more indicative of short range increases in the oxygen-transfer efficiency caused by the ingestion of the RSO Compound, either at the lungs or in the tissues. It may also be indicative of an increased efficiency in ridding the body of excess lactic acid. This would indicate that the RSO Compound would be most effective taken directly before exercise.

Thus, the RSO Compound balanced set of redox-signaling molecules is non-toxic (comparable to salt water) in all forms of application, anti-inflammatory, increases the production and efficiency of Glutathione Peroxidase and Superoxide Dismutase, as well as increase the efficiency of cells during athletic performance. The formulation is a safe native stabilized redox-signaling compound suitable for oral consumption.

DESCRIPTION OF THE DRAWINGS

FIG. 1 is a graph graph comparing $VCO_2$ to $VO_2$

DESCRIPTION OF THE ILLUSTRATED EMBODIMENTS

FIG. 1 is a graph comparing $VCO_2$ to $VO_2$. The amount of $O_2$ going in during aerobic exercise should be directly proportional to the $CO_2$ expelled; this is seen as a linear relation on the graph comparing $VCO_2$ to $VO_2$. The vertical axis shows the ml/min of $VCO_2$ and the horizontal axis shows the nil/min of $VO_2$ before RSO compared to after RSO. Both pre VT and post VT lines are fitted to the data. The significance of this data is discussed above.

Although this specification has referred to the illustrated embodiments, it is not intended to restrict the scope of the appended claims. The claims themselves recite those features deemed essential to the invention.

We claim:

1. A method for producing a balanced foundational redox-signaling oral (RSO) compound to enhance the efficiency and production of the body's native antioxidants and the performance of intercellular communications involved in the maintenance of healthy tissues and athletic performance, comprising:
   a. determining a balanced target mixture of chemical redox-signaling molecules for healthy cells and measuring concentrations of reactive molecules present using a combination of R-Phycoerythrin (R-PE), Aminophenyl Fluorescein (APF) and Hydroxyphenyl Fluorescein (HPF),
   b. electrochemically replicating this target mixture by:
   i. mixing an initial circulating saline solution,
   ii. adjusting the temperature, flow and sodium chloride concentration of the circulating saline solution at a level to prevent production of chlorates and regulate relative concentrations of resulting reactive molecules,
   iii. activating an electrochemical device to oxidize and reduce the circulating saline solution to produce a concentration and mixture of reactive molecules similar to those present in the target mixture by varying temperature, flow, pH, power-source modulation, salt homogeneity, and concentration parameters of the circulating saline solution to form an RSO compound, and
   c. verifying the similarity of the concentration of the redox-signaling molecules in the target mixture with those in the electrochemically replicated RSO compound to produce a verified RSO compound by using the combination of R-Phycoerythrin (R-PE), Aminophenyl Fluorescein (APF) and Hydroxyphenyl Fluorescein (HPF) used to measure the concentrations of reactive molecules present in the target mixture.

2. A method for producing a balanced foundational redox-signaling oral compound according to claim 1, wherein the combination of R-Phycoerythrin (R-PE), Aminophenyl Fluorescein (APF) and Hydroxyphenyl Fluorescein (HPF) is used for verification such that:
   i. a 2 micromolar concentration of R-PE loses 5%-50% of its fluorescence 6 hours after a 1:1000 solution of the RSO compound is added,
   ii. R-PE measurements indicate the same fluoroescence levels as a standard ROS generating solution of 0.2 or 1.0 mM AAPH,
   iii. APF measurements indicate the same relative amount as the target solution,
   iv. HPF measurements indicate a negligibly small reading,
   v. a pH of between 7.2 and 7.5, and
   vi. total chlorine concentration of less than 35 ppm by weight.

3. A method for producing a balanced foundational redox-signaling oral compound according to claim 1, including activating a fluid circulation device to maintain flow aging stratification and homogeneity of the circulating saline solution.

4. A method for producing a balanced foundational redox signaling oral compound according to claim 1, wherein the circulating saline solution has approximately 0.05% to 10% sodium chloride concentration by weight.

5. A method for producing a balanced foundational redox-signaling oral compound according to claim 1, wherein the combination of Aminophenyl fluorescein (APF) and Hydroxyphenyl fluorescein (HPF) is used for the detection of highly reactive oxygen species (hROS).

6. A method for enhancing an athletic performance characteristic, comprising:
   administering an RSO compound formed by activating an electrochemical device to oxidize and reduce a circulating saline solution to produce a concentration and mixture of reactive molecules similar to those present in a target mixture by varying temperature, flow, pH, power-source modulation, salt homogeneity, and concentration parameters of the circulating saline solution to form the RSO compound; and
   enhancing an athletic performance characteristic, wherein the method further comprises verifying the similarity of the concentration of the redox-signaling molecules in the target mixture with those in the RSO compound by analyzing measurements from a combination of R-Phycoerythrin (R-PE), Aminophenyl Fluorescein (APF) and Hydroxyphenyl Fluorescein (HPF) assays.

7. The method according to claim 6, wherein the measurements from the combination of R-Phycoerythrin (R-PE), Aminophenyl Fluorescein (APF) and Hydroxyphenyl Fluorescein (HPF) assays are used for verification such that:
   i. a 2 micromolar concentration of R-PE loses 5%-50% of its fluorescence 6 hours after a 1:1000 solution of the RSO compound is added,
   ii. R-PE measurements indicate the same fluoroescence levels as a standard ROS generating solution of 0.2 or 1.0 mM AAPH,
   iii. APF measurements indicate the same relative amount as the target solution,
   iv. HPF measurements indicate a negligibly small reading,
   v. a pH of between 7.2 and 7.5, and
   vi. total chlorine concentration of less than 35 ppm by weight.

8. The method according to claim 6, including activating a fluid circulation device to maintain flow aging stratification and homogeneity of the circulating saline solution.

9. The method according to claim 6, wherein the circulating saline solution has approximately 0.05% to 10% sodium chloride concentration by weight.

10. The method according to claim 6, wherein the combination of Aminophenyl fluorescein (APF) and Hydroxyphenyl fluorescein (HPF) is used for detection of highly reactive oxygen species (hROS).

11. The method according to claim 6, wherein the athletic performance characteristic is higher power output, longer time to ventilatory threshold, longer time to $VO_{2max}$, or increased efficiency of cells during athletic performance.

* * * * *